United States Patent
Rhodes (10) Patent No.: US 11,517,753 B2
(45) Date of Patent: Dec. 6, 2022

(54) INTERFERENTIAL TREATMENT WITH MODIFIED BEAT FREQUENCY

(71) Applicant: Donald A. Rhodes, The Woodlands, TX (US)

(72) Inventor: Donald A. Rhodes, The Woodlands, TX (US)

( * ) Notice: Subject to any disclaimer, the term of this patent is extended or adjusted under 35 U.S.C. 154(b) by 0 days.

(21) Appl. No.: 17/175,794

(22) Filed: Feb. 15, 2021

(65) Prior Publication Data

US 2021/0260376 A1    Aug. 26, 2021

Related U.S. Application Data

(60) Provisional application No. 62/979,350, filed on Feb. 20, 2020.

(51) Int. Cl.
| | |
|---|---|
| *A61N 1/00* | (2006.01) |
| *A61N 1/36* | (2006.01) |
| *A61B 5/01* | (2006.01) |
| *A61B 5/0531* | (2021.01) |
| *A61B 5/00* | (2006.01) |
| *A61N 1/04* | (2006.01) |
| *A61B 5/388* | (2021.01) |

(52) U.S. Cl.
CPC ............ *A61N 1/36031* (2017.08); *A61B 5/01* (2013.01); *A61B 5/0531* (2013.01); *A61B 5/388* (2021.01); *A61B 5/4035* (2013.01); *A61B 5/4836* (2013.01); *A61B 5/6804* (2013.01); *A61N 1/0456* (2013.01); *A61N 1/0484* (2013.01)

(58) Field of Classification Search
CPC ........................... A61N 1/36031; A61B 5/388
USPC ......................................................... 607/62
See application file for complete search history.

(56) References Cited

U.S. PATENT DOCUMENTS

| | | |
|---|---|---|
| 5,540,736 A | 7/1996 | Haimovich |
| 5,995,873 A | 11/1999 | Rhodes |
| 6,826,429 B2 | 11/2004 | Rhodes |
| 8,515,551 B2 | 8/2013 | Rhodes |
| 9,061,145 B2 | 6/2015 | Rhodes |
| 9,333,348 B2 | 5/2016 | Rhodes |
| 10,342,977 B2 | 7/2019 | Raghunayhan |
| 10,456,573 B1 | 11/2019 | Feinstein |
| 10,485,977 B1 | 11/2019 | Feinstein |

(Continued)

FOREIGN PATENT DOCUMENTS

| | | |
|---|---|---|
| WO | WO2020006048 | 1/2020 |
| WO | WO2020186274 | 9/2020 |

*Primary Examiner* — Nicole F Lavert
*Assistant Examiner* — Nicole F Johnson
(74) *Attorney, Agent, or Firm* — G. Turner Moller Jr.

(57) ABSTRACT

An electrical interferential technique is used to determine operable treatment parameters which are then used to apply a treatment to a patient. A range of beat frequencies is applied to the patient and an indicator of autonomic nervous system activity is measured. When some degree of autonomic nervous system activity is detected, a subsequent trial is conducted using an overlaying range of frequencies, a narrower range or a single frequency, in an attempt to fine tune the reaction of the autonomic nervous system. The subsequent trial may use a different measure of activity of the autonomic nervous system. A garment having a series of electrode sites thereon may be used for a partially trained person to correctly apply electrodes to the patient's body. The treatments may be conducted while the patient is asleep.

22 Claims, 4 Drawing Sheets

(56) References Cited

U.S. PATENT DOCUMENTS

| | | | |
|---|---|---|---|
| 10,493,272 B1 | 12/2019 | Feinstein | |
| 10,561,839 B2 | 2/2020 | Wong | |
| 10,682,512 B1 | 6/2020 | Feinstein | |
| 2007/0298895 A1 | 12/2007 | Johnson | |
| 2011/0105916 A1* | 5/2011 | Rhodes | A61B 5/02405 |
| | | | 600/509 |
| 2015/0297888 A1* | 10/2015 | Rhodes | A61B 5/4035 |
| | | | 607/62 |
| 2016/0317383 A1 | 11/2016 | Stanfield | |
| 2018/0028809 A1* | 2/2018 | Ziv | A61B 5/02405 |
| 2019/0240468 A1* | 8/2019 | Yun | A61N 1/36017 |

* cited by examiner

INTERFERENTIAL TREATMENT WITH MODIFIED BEAT FREQUENCY

This application is based, in part, on Provisional Application Ser. No. 62/979,350, filed Feb. 20, 2020, the disclosure of which is incorporated herein by reference and priority of which is claimed.

This invention relates to an improved technique for practicing an interferential therapeutic approach and more specifically to a technique for modifying the selection of the beat frequency, for simplifying and improving the placement of electrodes and conducting interferential treatments while the patient is asleep.

BACKGROUND OF THE INVENTION

There are a variety of therapeutic approaches that incorporate the application of electricity to a patient's body. One of these approaches is called interferential treatment which is described in some detail in U.S. Pat. Nos. 5,995,873; 6,826,429; 8,515,551; 9,061,145 and 9,333,348, the disclosures of which are incorporated herein by reference. The basic approach is to apply electrodes at various places on the human body and deliver pulses of electricity through the electrodes. Two, three or four pairs of electrodes are typically used in an interferential treatment. Each electrode is placed adjacent a nerve ending, an acupuncture point or a reflexology point of the patient, often on a foot or hand. The interferential treatment includes delivering a carrier frequency and a beat frequency through the electrodes. The result is a stream of pulses delivered to the nerve endings. Although the current approach is to use a carrier frequency and a beat frequency to produce beats which are the difference between the carrier and beat frequency, as used herein, interferential treatments comprise applying beats or pulses, however produced. The effectiveness of the interferential treatment is measured in a suitable manner. One simple effective approach to measure short term success is to measure the temperature of the patient's hand, foot or digits. Increased measured temperature is a proxy for increased blood circulation which is related to the effectiveness of the interferential technique. The measure of long term success is, of course, relief from pain or the ailment suffered by the patient. Long term success is the goal but, to get there, short term success comes first.

The problem is to select a combination of electrode placement and beat frequency that delivers an effective treatment. There are tens of thousands of combinations of electrode placements and beat frequencies to use in an electrical interferential treatment regimen. Invariably some combination of electrode placement and beat frequency are better than other combinations. Experimentation is necessary to determine workable electrode placements and beat frequencies because the measured response varies from patient-topatient and from time-to-time with the same patient. If a combination of electrode placement and one range of beat frequencies does not achieve an increased temperature response, the electrode placement is changed or the range of beat frequencies is changed. This process is repeated until a satisfactory response is obtained. The selection of an acceptable combination of electrode pattern and beat frequency is complicated by the vast multitude of electrode placements and beat frequencies plus the production of inconsistent selections and inconsistent patient response to the same selection of electrode placement and beat frequency.

SUMMARY OF THE INVENTION

The disclosed technique involves adjusting the beat frequency selection in response to another parameter which varies in a manner differently than a normally used parameter which is a proxy for the effectiveness of an electrical interferential treatment regimen. The normally used parameter may be skin temperature which is a proxy for increased blood circulation which is one measure of the effectiveness of an interferential treatment regimen. The other parameter may be skin impedance or any other indicator of autonomic system activity. Skin impedance is measured in any suitable manner, such as disclosed in an article entitled Skin Impedance Measurements Using Simple and Compound Electrodes, Med. & Bio. Eng. & Comput., 1992 p 97-102 by E. J. Woo et al.

After selection of a range of beat frequencies and an electrode pattern that produces some increase in measured temperature, the beat frequency is narrowed using measurements of skin impedance as a guide. For example, if the range of beat frequencies is 1-10 and a small positive temperature increase is noted, for example one half degree F., the range may be narrowed to 4-8 beats applied to the patient to determine whether skin impedance increases from the previous selection. In one sense, the narrowed range of beat frequencies lies wholly within the first range but, in other sense, the narrower range of frequencies overlays the first range. It may be that attempting to narrow the beat frequency range will indicate that the upper or lower end of the range is more effective, leading to selecting a beat frequency range that includes part of the original range and part of an adjacent range, i.e. the second range may extend past one end of the first range. There appears to be a short term increase in skin impedance followed by a long term decrease in skin impedance. The advantage of tracking skin impedance is that virtually instantaneous results are obtained. This also allows the intensity of the treatment to be increased or decreased while the treatment is occurring. If skin impedance does temporarily increase the range may be further narrowed to 5-6 beats and the process repeated to determine its effectiveness.

When trials or treatments are conducted by the patient or a relatively untrained caregiver, the placement of electrodes is often haphazard so it may be desirable to provide a guide or template that can be used to place electrodes properly. This can be accomplished by a garment worn by the patient having indicia designating the desired electrode location. Because there are many potential electrode sites, many different garments may be provided or many different patterns may be employed to transfer the desired electrode placement to a garment.

It may be desirable with some patients to conduct treatments while the patient is asleep. This has the advantage of potentially longer treatments or different treatments at a time when the body's healing apparatus is already working.

It is an object of this invention to provide a technique for narrowing the beat frequency selection in an electrical interferential treatment process.

A further object of this invention is to provide an approach for narrowing the beat frequency selection by incorporating inputs from more than one indicator of autonomic nervous system activity.

Another object of this invention is to provide a guide or template for placing electrodes correctly.

A more specific object of this invention is to provide a garment having indicia applied to the garment to indicate the location to place electrodes.

A further object of this invention is to provide a method and apparatus for treating a sleeping patient.

Other objects and advantages of this invention will become apparent as this description proceeds, reference being made to the accompanying drawings and appended claims.

DETAILED DESCRIPTION OF THE INVENTION

Figure 1:
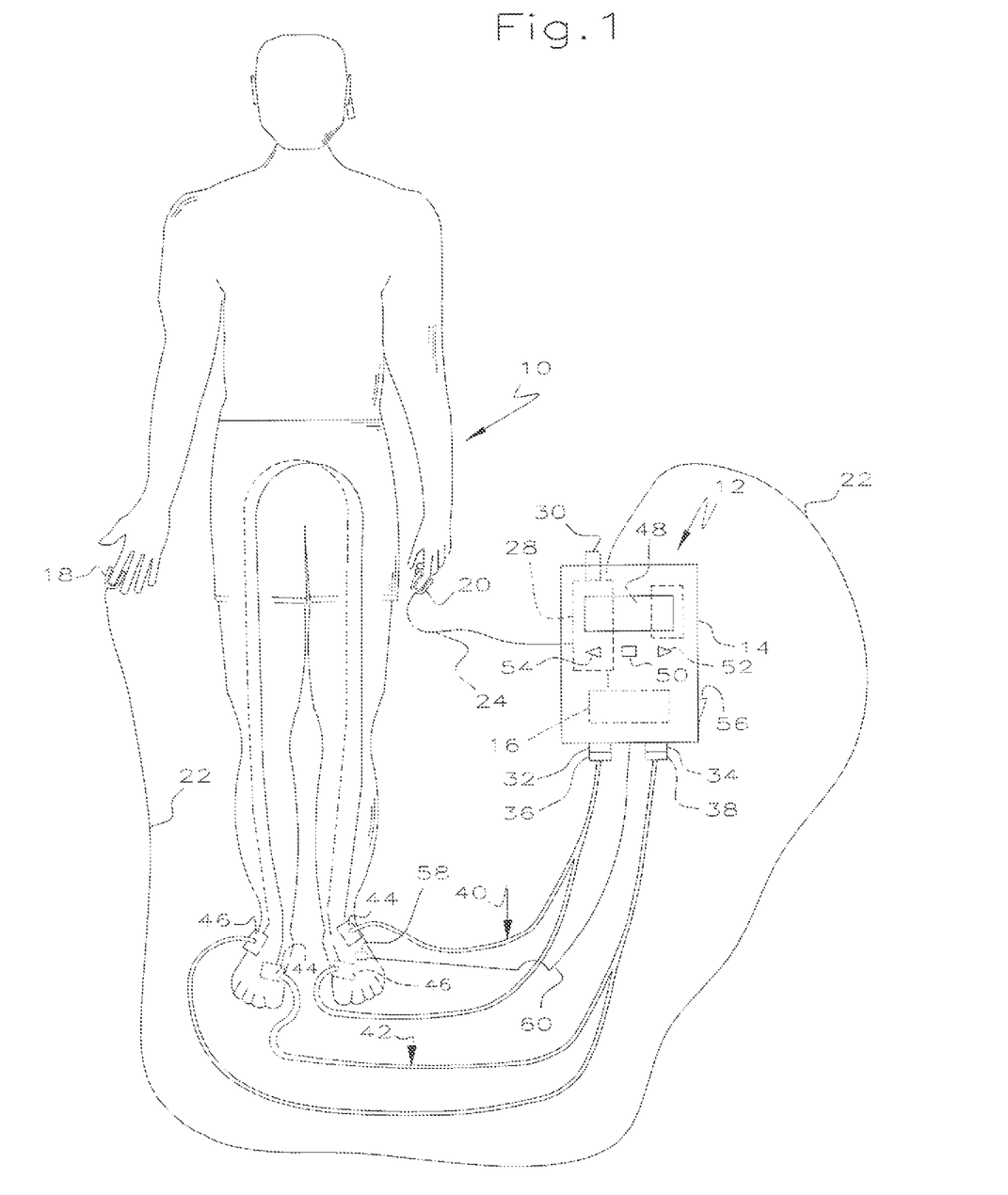
FIG. 1 is a schematic view of an interferential treatment device deployed on a patient.

Referring to FIG. 1, a patient 10 is hooked up to an electrical interferential therapy device 12 inside a housing 14. The electrical interferential therapy device 12 may include a more-or-less conventional treatment module 16 such as is commercially available from Alan Neuromedical Technologies LLC of The Woodlands, Tex. to which reference is made for a more complete description thereof.

A wide variety of parameters may be used to monitor the autonomic nervous system and thereby determine the effect of an interferential treatment on the patient. These parameters may include skin impedance or resistivity, peripheral skin temperature, pulse rate, blood pressure, iris pupil diameter, respiration rate, blood oxygen content or any other indicator of autonomic nervous system function as stated in U.S. Pat. No. 8,515,551. Measuring skin temperature has proven to be an advantageous selection because it is unambiguous, reliable and easy to determine by commercially available sensors. Although temperature may be taken at any suitable location, a toe or finger have proven easy and effective. Any other indicator of autonomic nervous system function may alternately be used as a primary parameter, such as skin impedance or resistivity, pulse rate, blood pressure, iris pupil diameter, respiration rate, blood oxygen content or any other indicator of autonomic nervous system function. The secondary parameter, used to fine tune beat frequency selection, is different from the primary parameter and may be another of the indicators of autonomic nervous system function, and may preferably be one that does not exactly mimic the reaction of the primary parameter.

Using digit temperature as the primary parameter, one or more sensors 18, 20 which may preferably be a digital temperature sensor incorporated into a spring biased clip which may attach to a finger or toe on either or both sides of the patient 10. The sensors 18, 20 may connect by a wire 22, 24 to a module 28 in the housing 14. The module 28 may be a data processor to record the temperature sensings from the sensors 18, 20, store the values in a memory module 30, control the treatment module 16, otherwise operate the device 12 and may transmit any data, stored or unstored, to a suitable storage location such as the cloud. Other sensors are equally effective and under some conditions, more so. A temperature sensor sewn into a garment would be particularly desirable when the patient is undergoing treatment when asleep or conducting normal daily activities. Similarly, wire or braided wire embedded or woven into a garment would be suitable.

The housing 14 may include a series of receptacles 32, 33, 34, 35 capable of accepting a jack 36, 37, 38, 39 of insulated wire pairs 40, 41, 42, 43 leading to electrode pairs 44, 44', 45, 45', 46, 46', 47, 47'. A suitable display 48 provides readings such as values from the sensors 18, 20, the carrier frequency, the pulse frequency or frequency ranges being tested, the time and date of the procedure and other desirable information, such as the intensity of treatment, patient data, time left to finish the treatment, time elapsed during a particular testing cycle, results of testing sequences and whether it is time to replace the electrodes. The device 12 may be battery powered which can allow treatment while the patient sleeps or by wearing the unit during the day.

Standard commercially available electrical interferential treatment devices have either a fixed carrier frequency or a minimally selectively variable carrier frequency. For reasons which are mainly historical, these frequencies are conventionally 1850 Hz and 2850 Hz in the Sympathetic Therapy System from Dynatronics, Inc. or 4000 Hz in a device commercially available from Rehabilicare Corporation of St. Paul, Minn.

The device 12 may include a select actuator 50 and up/down actuators 52, 54. In prior art devices, intensity can only be set at the beginning of a treatment. An advantage of the current approach is the data processor module 28 can change the intensity of the pulses delivered through the electrodes in the middle of a treatment regimen in response to the number of pulses delivered, the elapsed time of treatment, the preference of the patient, the response of the treatment as measured by one of the parameters and the like. The module 28 may provide other functions. For example, the electrodes 44, 44', 46, 46' don't provide good sensings indefinitely. The module 28 may run tests to determine whether the electrodes need to be replaced, may count the number of treatments or the number of parameter determining trials are run and display a message on the screen 48 to replace the electrodes. In response to such a message, the select actuator 50 may be depressed to send a message to the module 28 that the electrodes have been or will be changed. The device 12 may also include a timer function and the time of and duration of treatments and/or the acquisition of treatment parameters. The device 12 may also include an on-off switch 56. The device 12 may preferably be battery powered thereby enabling the patient to undergo treatment when asleep and, if the device 12 is small enough, to undergo treatment while walking, driving or in the conduct of normal daily activities.

The carrier and beat frequencies used in selecting treatment parameters may be selected by the actuators 50, 52, 54 or default selections may be provided by software in the processor 28. Experience has shown that the vast majority of desirable beat frequencies are between 1-150 beats per second (bps) although current commercially available devices only employ 1-80 beats per second. In attempts to find an effective beat frequency in a reasonable time frame, this range has been subdivided into segments of a small fraction of 1-150 Hz, typically 1-10 bps, 11-20 bps, 21-30 bps, 31-40 bps etc. Experience has shown that some of the segments, of at least one carrier frequency where most efforts have been made, provide the most desirable beat frequency.

When it is desired to increase the treatment intensity, the increase actuator 52 is depressed at the outset of a treatment or in response to the processor module 28 during a treatment as discussed above. It will accordingly be seen that the device 12 includes a circuit for delivering therapeutic electrical energy into the body of the patient and more particularly includes a subcircuit for modifying the carrier frequency, the beat frequency and/or the amplitude of alternating current type energy.

The electrodes are attached to the patient's skin or to a garment as explained hereinafter, i.e. they may be self adherent. The location of the electrodes on the patient establishes the electrical circuit in the patient's body. As shown in FIG. 1, in one electrode pattern, one electrode 44 is placed adjacent the end or terminus of the right medial planar nerve L5 and its matching electrode or mate 44' is placed adjacent the end or terminus of the left sural nerve S1, inferior to the left ankle bone (lateral malleolus) thereby establishing a first electrical circuit in the patient's body. As used herein, the terms L5, S1 and the like are standard medical terminology for nerves in the human leg. The electrode pattern in FIG. 1 is shown in U.S. Pat. No. 5,995,873, to which reference is made for a more complete description. It will be understood there are hundreds or thousands of potential electrode patterns using different number of electrode pairs. In addition to the L5, S1 pattern, a preferred approach may be to use an additional four electrodes for a total of eight. The additional electrodes may be placed in any suitable manner, such as in an L4, S2, L5-L4 pattern. Those skilled in the art will recognize this description as representative of commercially available electrical interferential treatment devices available from Alan Neuromedical Technologies LLC of The Woodlands, Tex.

In order to adjust the selection of the beat frequency, two of the indicators of autonomic nervous system activity are used together. For example, if skin temperature is used as the primary indicator of effectiveness of the interferential treatment, skin impedance or resistance may be used as a secondary indicator to modify the beat selection by adjusting the beat selection from one range to a narrower or wider range or to a single number. For example, in a trial to determine an effective combination of electrode placement and beat frequency, one may start with a given electrode placement and a range of beat frequencies. The normal or default setting for beat frequencies has been 1-10. After achieving some temperature response, the beat frequency may be narrowed in response to readings from a skin impedance or resistance sensor 58 connected by a wire or communication link 60 to the unit 12. These adjustments may preferably be made by software in the module 28 or manually by the user. The impedance sensor 58 may preferably be near one pair of the electrodes, for example on the same hand, foot or limb. Over time, the response to interferential treatment as measured by skin temperature tracks the response as measured by skin impedance. An advantage of using skin impedance is that changes in skin impedance occur and can be measured in a matter of seconds while changes in skin temperature occur and can be measured in a matter of minutes. Thus, when narrowing adjustments to beat frequency are made in response to skin impedance and the narrowed range produces an improved response, skin impedance increases in the short term, and will be verified several minutes later by skin temperature rises. This process of narrowing the range of beat frequencies may be repeated to again modify the skin temperature response. For example, with a default beat frequency range of 1-10 beats/second, a first narrowed range may be 2-8 beats/second, a second narrowed range may be 4-6 beats/second and a third narrowed range may be 4.5-5.5 beats/second.

The situation in electrical interferential treatment is to find a combination of electrode placement and beat frequency that produces an adequate temperature response. In the past, this has typically been done by changing the electrode placement or by changing from beat selection from a default range of 1-10 to ranges of 11-20, 21-30 and so on. In contrast and in some approaches of this invention, the idea is to find a temperature response that may be inadequate and then attempt to fine tune the beat frequency in response to another parameter such as skin resistivity or impedance. As used herein, impedance is defined either as resistance, impedance or resistance and impedance.

There are many possible variations in the generation of beat frequencies. The current standard approach for a beat frequency selection of 1-10 beats/second, for example, is to apply the beats in a pattern, e.g. 1, 2, 3, 4, 5, 6, 7, 8, 9, 10, 10, 9, 8, 7, 6, 5, 4, 3, 2, 1 and then repeat. The current standard pattern for 11-20 beats/second is 11, 12, 13, 14, 15, 16, 17, 18, 19, 20, 20, 19, 18, 17, 16, 15, 14, 13, 12, 11 and then repeat. Similarly, the restricted beat frequency range may be in any suitable pattern, e.g. 4, 5, 6, 7, 7, 6, 5, 4, if results from the sensor 58 dictates a range of 4-7 or 9, 10, 11, 12 in the event trials indicate the more desirable beat frequency range overlaps a standard segment. Although these patterns are standard, the pattern used in the practice of the disclosed treatment may be of any suitable description.

There are some circumstances when the most effective treatments are in a fairly narrow temperature range. This means there are situations where there may be too little temperature response and too much. For example, many patients with Complex Regional Pain Syndrome and erythromelalgia may be better treated with temperature responses in the range of 1-2 degrees F. Although a preferred technique for degrading temperature performance is to decrease the intensity of the treatment, as by reducing the amplitude of the carrier and beat frequencies, it is accordingly one advantage of this invention to fine tune the beat frequency to reduce the temperature response by widening the range of beat frequencies to overlap the original range of beat frequencies, which means the second beat frequency range extends beyond the original range. This is in contrast to current belief that a temperature response of 1-3, degrees F. is thought to be most desirable. Consequently, the beat frequency may be altered in an attempt to increase or decrease the sensed temperature response.

What constitutes an adequate temperature response is discussed in some length in U.S. Pat. No. 9,061,145 to which reference is made for a more complete understanding of adequate and inadequate temperature responses. If the temperature response is adequate, treatment of the patient follows, either automatically in response to a command by the data processor 28 or manually in response to a command by the patient or care giver.

The various parameters of effectiveness include skin impedance, skin resistivity, peripheral skin temperature, pulse rate, blood pressure, iris pupil diameter, respiration rate, blood oxygen level or any other indicator of autonomic nervous system function. These parameters do not give identical responses to the same combination of electrode placement and beat frequency and do not have otherwise identical characteristics, e.g. cost, ease of use, reliability, repeatability, relative lack of ambiguity and the like. As disclosed above, a workable combination of parameters is peripheral skin temperature and skin impedance or resistivity which has the advantage of low cost, reliable relatively unambiguous peripheral skin temperature and low cost, rapid response of skin impedance or resistivity. Other combinations of parameters are operable and have their advantages because they have different responses to the same interferential treatment, different response times, different costs, different difficulties of use and other differences.

Figure 2A:
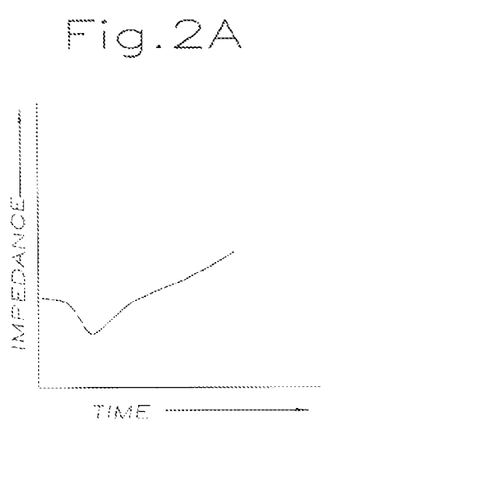
FIG. 2a is a graph of skin impedance over time showing an improved interferential response.
Figure 2B:
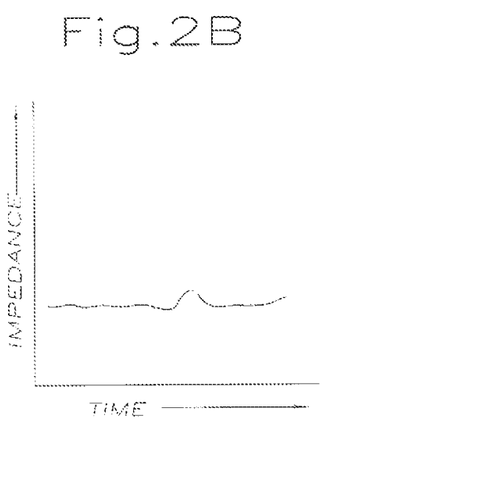
FIG. 2b is a graph of skin impedance over time showing no improvement in response to an interferential treatment.

FIG. 2a shows a graph of skin impedance versus time showing an initial short term decrease in skin impedance followed by a longer term response where skin impedance increases. This type response typically shows an improved response to interferential treatment. FIG. 2b shows a graph of skin impedance versus time showing no change in skin impedance and consequently no change in response to interferential treatment. The time interval expressed in FIG. 2a is usually on the order of less than one minute. Although skin impedance is quicker acting than skin temperature, skin temperature tracks skin impedance in a few minutes so it may be advantageous to wait until skin temperature corroborates skin impedance measurements before modifying the beat frequency range. In one situation, adjusting the beat frequency range is done in response to skin impedance and, in the other situation, is done in response to skin temperature.

Figure 3:
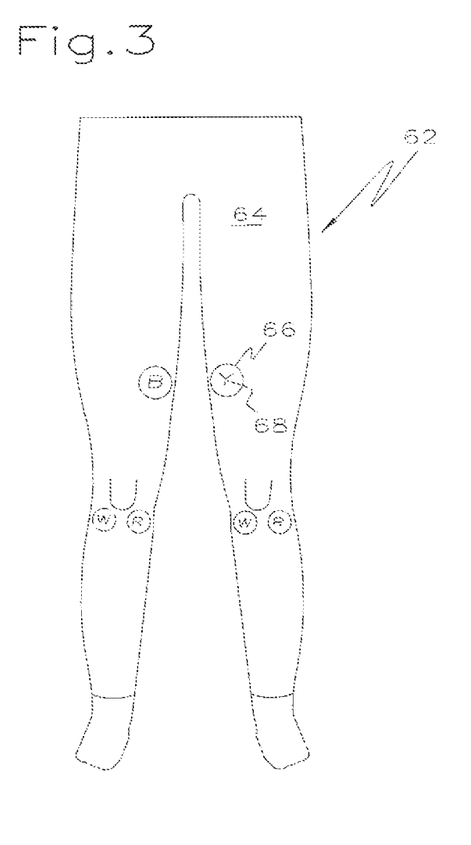
FIG. 3 is a front view of a pair of pants having indicia thereon indicating one preferred electrode location.
Figure 4:
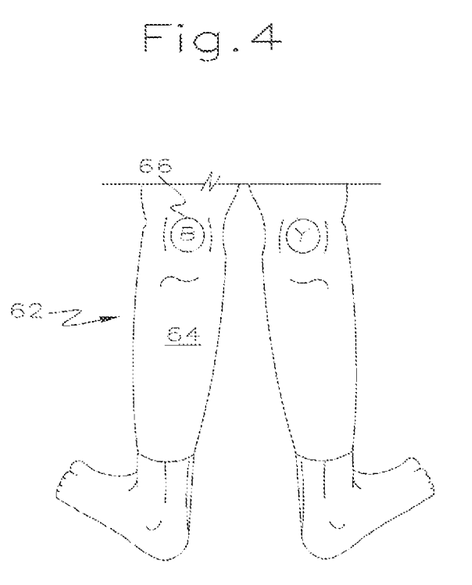
FIG. 4 is a partial back view of the pants of FIG. 3.

Referring to FIGS. 3 and 4, there is illustrated a garment or pants 62 of a fabric 64 having thereon a series of sites or locations 66 where electrodes are to be placed in a commonly used electrode pattern. The sites 66 may be applied to the garment fabric 64 in any suitable manner. As illustrated, the pattern of electrodes is a common effective eight electrode pattern. This illustrated pattern is exemplary only and many different patterns using different numbers of electrodes are feasible. The electrodes 44, 44', 46, 46' may be applied directly to the fabric 64 of the garment 62 or the locations 66 may comprise a hole in the fabric 64 but coded around the hole as will be apparent hereinafter so the electrodes may be applied directly to the patient's skin.

The electrode pattern on the garment 62 is conveniently illustrated to be coded so indicia 68 at the site 66 correspond to a similar number on the electrode or electrode wire shown in FIG. 1. Any suitable technique may be used.

Figure 5:
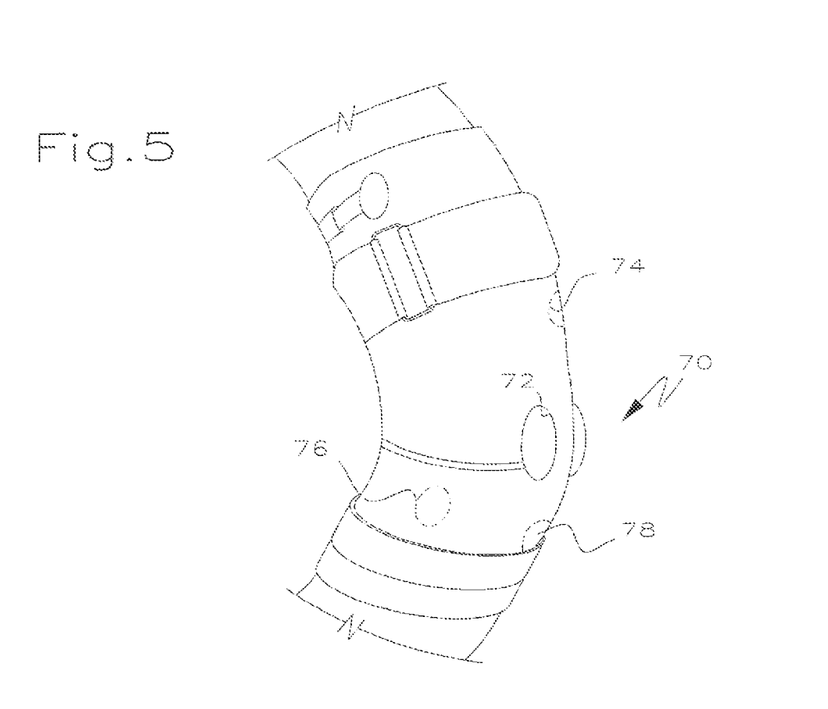
FIG. 5 is a photograph of another garment useful as a guide for electrode placement.
Figure 6:
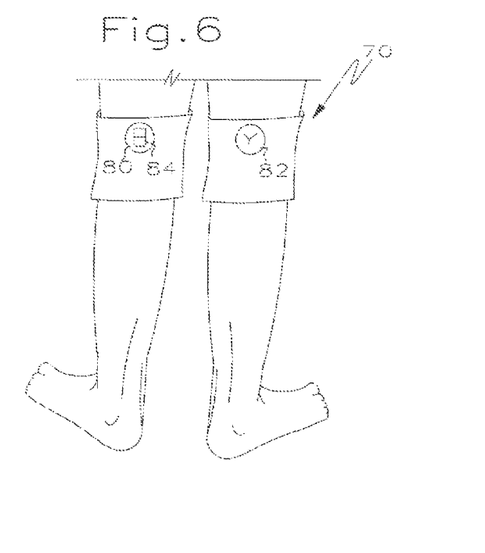
FIG. 6 is a back view of the knee brace shown in FIG. 5 illustrating the knee brace on a patient and illustrating the sites where electrodes are to be placed in one common electrode pattern.
Figure 7:
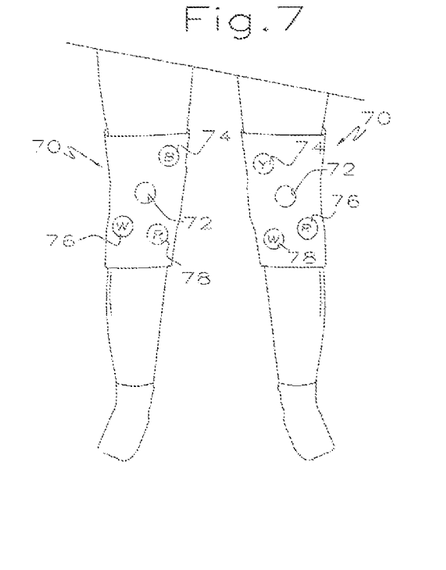
FIG. 7 is a front view, similar to FIG. 6, illustrating the sites where electrodes are to be placed in one common electrode pattern.

Referring to FIGS. 5-7, there is illustrated one commonly used electrode pattern incorporated into a knee brace 70 providing another example of a garment which may be used to locate electrodes in an appropriate location. The knee brace 70 includes an opening 72 which is placed over the kneecap of the wearer and thereby position the brace in repeatable positions. The electrodes 74, 76, 78 may be sewn into the brace 70 on the front of the knee brace and electrodes 80, 82 may be sewn on the back and suitable wires or communication links (not shown) provided connecting the electrodes to the module 28. In the alternative, indicia may be provided on the brace 70 to indicate an electrode placement. Similar VELCRO wraps may be used on the hand, using the thumb as an anatomical landmark, or may be used on the foot and ankle using the ankle bones as an anatomical landmark to position the wrap correctly. The electrode pattern on the knee brace 70 is conveniently illustrated to be coded so indicia 84 at the electrode sites correspond to a similar number on the electrode or electrode wire shown in FIG. 1. Any suitable technique may be used.

Figure 8:
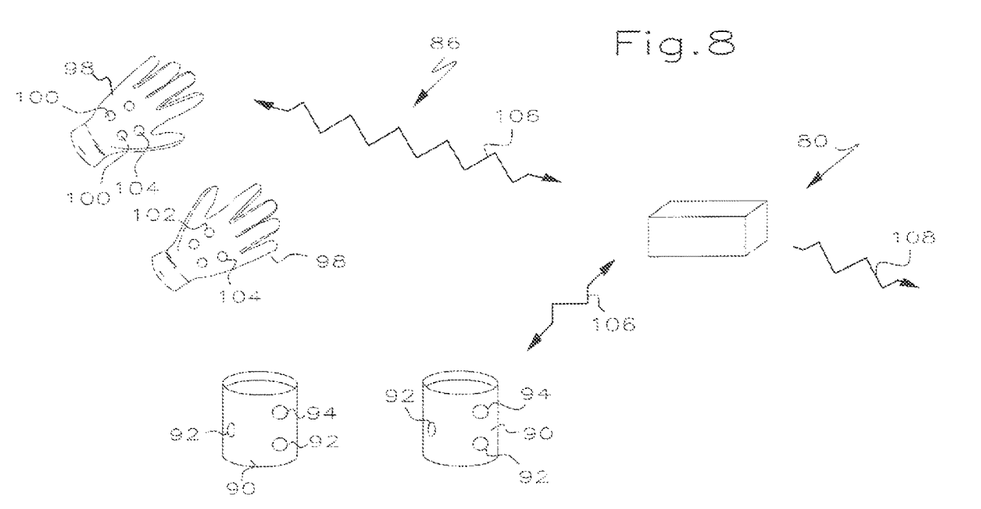
FIG. 8 is a view of a device to conduct interferential trials and interferential treatments while a patient sleeps.
Figure 9:
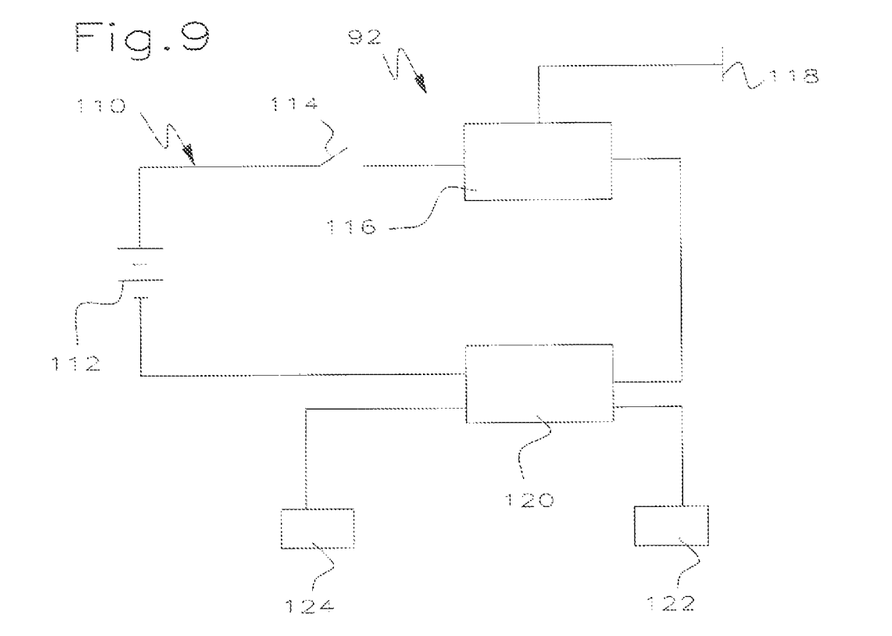
FIG. 9 is a schematic view of an electrode assembly of FIG. 8.

Referring to FIGS. 8-9, there is illustrated another electrical interferential system 86 that looks much different than FIG. 1 but which operates similarly. The system 86 includes a control module 88 which may be placed on a bedside table of the patient and one or more bodily worn garments 90. The control module 88 may be battery powered or conventionally powered through household electrical connections. Some of the bodily worn garments may be such as shown in FIGS. 3-7 to which electrode assemblies are attached at the designated locations and to which is attached a suitable primary sensor 94 such as a skin thermometer and a suitable secondary sensor 96 such as a skin impedance sensor. In the alternative, or in addition, the bodily worn garments may include a pair of gloves or wrist bands 98 to which are attached electrode assemblies 100 and a primary sensor 102 and may include a secondary sensor 104 such as a skin impedance sensor. The control module 88 and the garments 90, 98 may include a wireless communication system 106 so the control module 88 can send wireless signals to the electrode assemblies 90, 98 and receive information from the sensors 94, 96, 102, 104. In addition, the system 86 includes a communication system 108 communicating with a receiver so the data recovered from the sensors 94, 96, 102, 104 and other suitable information can be saved for later viewing by the patient or medical personnel. Currently, the cloud may be a preferred location for data storage but this depends on future developments.

An exemplary electrode assembly 92 is shown in more detail in FIG. 9 and includes a circuit 110 including a battery 112, a wireless operated on-off switch 114, a beat generator 116 delivering pulses to an electrode 118 in communication with the skin of the patient and a short distance communication device 120. The circuit 110 also includes a primary sensor 122 for detecting a response of the autonomic nervous system and a secondary sensor 124 for adjusting the range of beat frequencies in response to a secondary indicator of autonomic system response. As in the embodiment of FIG. 1, the primary sensor 122 may be a skin temperature sensor and the secondary sensor 124 may be a skin impedance sensor. The control module 88 adjusts the range of beat frequencies applied by the electrodes 118 in response to information from the secondary sensor 124.

An important advantage of the system of FIGS. 8-9 is the ability to treat the patient while asleep. Not only does this allow for longer treatment times but also allows for the application of different treatments. It may be preferred that a lower body garment is placed on the knees or feet of the patient and an upper body garment 90, 98 placed on the hands or wrists of the patient. A lower body treatment would be followed by an upper body treatment. The module 88 would then turn off the electrode assemblies 92, 100 and after a suitable wait, repeat the upper and lower body treatments.

Lower and upper body treatments tend to create more of one neuropeptide and less of another. When combined, the lower and upper body treatments combine to overcome the deficiencies of each other and make a good combination. One approach that may be preferred is to conduct upper and lower body treatments when the patient is asleep, thereby affording time for multiple approaches. One approach is to conduct an upper and a lower body treatment followed by a delay of several hours and then conduct another upper and lower body treatment. Another approach is to conduct a trial in the middle of a treatment by again adjusting the beat frequency and determining whether the response from the primary and/or secondary sensors shows an improvement. Operation of the system 86 commences when the patient has placed the garments 90, 98 in their appropriate locations so the electrodes are located at their desired sites. The control module 88 is turned on and includes some mechanism to determine whether the patient is asleep. This may be simply a timer, may be a more sophisticated head attached device used in sleep clinics or may be something intermediate such as a motion sensor equipped with software to realize the patient isn't moving much. The system 86 is turned on and the sleep recognizer detects when the patient is asleep. The module 88 then signals the beat generators 116 to deliver a range of beat frequencies to the electrodes 118, detects responses from the sensors 122, 124 and adjusts the range of beat frequencies accordingly.

In good health, the analogous fingers of the left and right hands show a temperature variation of less than 1° F. no matter what the ambient temperature is. The hand that is colder is usually due to the prevalence of norepinephrine which diminishes the circulation in the cold hand. Interferential treatments often normalize the left/right differential and demonstrate an improvement in the patient.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention.

I claim:

1. A device configured to deliver an electrical interferential treatment, comprising
a series of electrodes configured to be applied to a patient; and
a system configured to deliver beats from a spectrum of beat frequencies through the electrodes;
the system being configured to divide the spectrum of beat frequencies into a series of frequency bands;
the system being configured to deliver beat frequencies in a first range in a selected one of the frequency bands;
the system being configured to measure effectiveness of the beat frequencies in the first range by measuring a first parameter of autonomic nervous system activity and thereby determine a level of autonomic nervous system activity in the first range of beat frequencies;
the system being configured, in response to a predetermined value of the first parameter, to deliver a beat frequency in a second range of beat frequencies, the second range of beat frequencies being narrower than the first range and including at least some beats inside the first range; and
the system being configured to measure effectiveness of the beat frequencies in the second range by measuring a second parameter, different than the first parameter, of autonomic nervous system activity during the delivery of the second range of beat frequencies, the second parameter being configured to provide a measurable value at a rate different than the first parameter.

2. The device of claim 1 wherein the second range of beat frequencies is wholly within the first range of beat frequencies.

3. The device of claim 1 wherein the second range of beat frequencies extends past one end of the first range of beat frequencies.

4. The device of claim 1 wherein the first parameter is skin temperature and the second parameter is skin impedance.

5. The device of claim 1 wherein the second range of beat frequencies is a single value.

6. The device of claim 1 further comprising a first set of garments configured to be attached to lower limbs of a patient, a second set of garments configured to be attached to upper limbs of a patient, the electrodes being attached to the garments and configured to receive interferential beats, and the system being configured to deliver the beat frequency to the first set and to the second set of garments.

7. The device of claim 1 wherein the first range of beat frequencies is a small fraction of 1-150 Hz.

8. The device of claim 1 wherein the first parameter and the second parameter are selected from skin impedance, skin resistivity, peripheral skin temperature, pulse rate, blood pressure, iris pupil diameter, respiration rate and blood oxygen content.

9. The device of claim 1 wherein the first range of beat frequencies is wholly within the selected one of the frequency bands.

10. A method of interferential treatment, comprising
applying electrodes to a patient and delivering a first range of beat frequencies to the electrodes, the first range of beat frequencies being taken from a selected one of a series of bands of frequencies, measuring effectiveness of the beat frequencies in the first range by measuring a first parameter of autonomic nervous system activity and thereby determining a level of autonomic nervous system activity in the first range of beat frequencies;
in response to a predetermined value of the first parameter, modifying the level of autonomic nervous system activity by adjusting the beat frequency to a second range of beat frequencies, the second range being narrower than the first range and including at least some beats inside the first range; and
measuring a second parameter of autonomic nervous system activity, different than the first parameter, the second parameter being configured to provide a measurable response at a different rate than the first parameter.

11. The method of claim 10 wherein the first parameter is skin temperature and the second parameter is skin impedance.

12. The method of claim 10 wherein, during an interval in a treatment, applying a third range of beat frequencies through the electrodes, measuring a third parameter, different than the first and second parameters, of autonomic nervous system activity and determining a third level of autonomic nervous system activity, the third range of beat frequencies being within the second range of beat frequencies and modifying the treatment to the patient by including the third range of beat frequencies.

13. The method of claim 10 further comprising applying a treatment to the patient including the second range of beat frequencies.

14. The method of claim 10 wherein the first range of beat frequencies is a small fraction of 1-150 Hz.

15. The method of claim 10 wherein at least some of the electrodes are located on a limb of the patient, the second parameter is skin impedance and the second parameter is measured on the same limb as the at least some of the electrodes.

16. The method of claim 10 wherein the first parameter and the second parameter are selected from skin impedance, skin resistivity, peripheral skin temperature, pulse rate, blood pressure, iris pupil diameter, respiration rate and blood oxygen content.

17. A device configured to deliver an electrical interferential treatment, comprising
   a series of electrodes configured to be applied to a patient; and
   a system configured to deliver beats in a spectrum of beat frequencies through the electrodes;
   the system being configured to divide the spectrum of beat frequencies into a series of frequency bands;
   the system being configured to deliver beat frequencies in a first range in a selected one of the frequency bands;
   the system being configured to measure effectiveness of beat frequencies in the first range by measuring a first parameter of autonomic nervous system activity and thereby determine a level of autonomic nervous system activity in the first range of beat frequencies;
   the system being configured, in response to a predetermined value of the first parameter, to deliver a beat frequency in a second range of beat frequencies, the second range being narrower than the first range and including at least some beats inside the first range.

18. The device of claim 17 wherein the second range of beat frequencies is wholly within the first range of beat frequencies.

19. The device of claim 17 wherein the second range of beat frequencies extends past one end of the first range of beat frequencies.

20. The device of claim 17 wherein the system is configured to adjust the range of delivered beat frequency in response to the second parameter.

21. The device of claim 17 wherein the system is configured to apply a treatment to the patient using the second range of beat frequencies when the second parameter indicates an increased reaction by the autonomic nervous system.

22. The device of claim 17 wherein the first parameter and the second parameter are selected from skin impedance, skin resistivity, peripheral skin temperature, pulse rate, blood pressure, iris pupil diameter, respiration rate and blood oxygen content.

* * * * *